United States Patent
Frazier et al.

(10) Patent No.: US 6,682,528 B2
(45) Date of Patent: *Jan. 27, 2004

(54) ENDOSCOPIC BIPOLAR ELECTROSURGICAL FORCEPS

(75) Inventors: Randel Alven Frazier, Louisville, CO (US); Michael John Lands, Palm Harbor, FL (US); Wade Lukianow, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/246,107

(22) Filed: Sep. 17, 2002

(65) Prior Publication Data

US 2003/0040745 A1 Feb. 27, 2003

Related U.S. Application Data

(63) Continuation of application No. 09/825,500, filed on Apr. 3, 2001, now Pat. No. 6,458,130, which is a continuation of application No. 09/177,950, filed on Oct. 23, 1998, now abandoned.

(51) Int. Cl.$^7$ ............................................. A61B 18/14
(52) U.S. Cl. ............................ 606/51; 606/46; 606/48; 606/207; 606/208
(58) Field of Search ............................. 606/46, 48–52, 606/170, 207, 208

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,176,479 A | 10/1939 | Willis |
| 2,305,156 A | 4/1942 | Grubel |

(List continued on next page.)

FOREIGN PATENT DOCUMENTS

| | | |
|---|---|---|
| CA | 2104423 | 2/1994 |
| EP | 0364216 A1 | 4/1990 |
| EP | 0518230 A1 | 12/1992 |
| EP | 0 541 930 B1 | 5/1993 |
| EP | 0584787 A1 | 3/1994 |
| EP | 0623316 A1 | 11/1994 |
| EP | 0650701 A1 | 5/1995 |
| EP | 0694290 A3 | 3/1996 |

(List continued on next page.)

OTHER PUBLICATIONS

US 6,090,109, 7/2000, Lands et al. (withdrawn)
Sigel et al. "The Mechanism of Blood Vessel Closure by High Frequency Electrocoagulation" Surgery Gynecology & Obstetrics, Oct. 1965 pp. 823–831.

(List continued on next page.)

Primary Examiner—Lee Cohen

(57) ABSTRACT

A endoscopic bipolar forceps for clamping and sealing tissue includes first and second jaw members pivotally attached in opposing relation relative to one another which are movable from a first open position wherein the jaw members are disposed in spaced relation relative to one another to a second clamping position wherein the jaw members cooperate to grasp tissue therebetween. A drive rod assembly connects each of the jaw members to a source of electrical energy such that the jaw members are capable of conducting bipolar energy through the tissue held therebetween. A handle attached to the drive rod assembly imparts movement of the first and second jaw members from the first and second positions. At least one stop member is attached to the jaw members for controlling the distance between the jaw members. The forceps may also include a yoke member for insulating the jaw members from one another to prevent short circuiting of the forceps. Preferably, the yoke member and jaw member interface is dimensioned to withstand the high shearing forces normally associated with sealing tissue.

8 Claims, 9 Drawing Sheets

U.S. PATENT DOCUMENTS

| | | |
|---|---|---|
| 2,632,661 A | 8/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| D276,790 S | 12/1984 | Laske |
| 4,552,143 A | 11/1985 | Lottick |
| 4,574,804 A | 3/1986 | Kurwa |
| 4,597,379 A | 7/1986 | Kihn et al. |
| 4,657,016 A | 4/1987 | Garito et al. |
| 4,671,274 A | 6/1987 | Sorochenko |
| 4,685,459 A | 8/1987 | Xoch et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,151,102 A | 9/1992 | Xamiyama et al. |
| 5,176,695 A | 1/1993 | Dulebohn |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Schaffer |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,496,317 A | 3/1996 | Goble et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,569,241 A | 10/1996 | Edwards |
| 5,571,100 A | 11/1996 | Goble et al. |
| 5,573,535 A | 11/1996 | Viklund |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,626,578 A | 5/1997 | Tihon |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,649,959 A | 7/1997 | Hannam et al. |
| 5,658,281 A | 8/1997 | Heard |
| 5,667,526 A | 9/1997 | Levin |
| 5,674,220 A | 10/1997 | Fox et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,727,428 A | 3/1998 | LeMaire, III et al. |
| 5,743,906 A | 4/1998 | Parins et al. |
| 5,755,717 A | 5/1998 | Yates et al. |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,792,137 A | 8/1998 | Carr et al. |
| 5,792,177 A | 8/1998 | Kaseda |

| | | |
|---|---|---|
| 5,800,449 A | 9/1998 | Wales |
| 5,810,808 A | 9/1998 | Eggers |
| 5,814,043 A | 9/1998 | Shapeton |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,891,141 A | 4/1999 | Rydell |
| 5,891,142 A | 4/1999 | Eggers et al. |
| 5,893,875 A | 4/1999 | O'Connor et al. |
| 5,902,301 A | 5/1999 | Olig |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,951,549 A | 9/1999 | Richardson et al. |
| 5,954,720 A | 9/1999 | Wilson et al. |
| 5,976,132 A | 11/1999 | Morris |
| 5,989,277 A | 11/1999 | LeMaire, III et al. |
| 6,004,335 A | 12/1999 | Vaitekunas et al. |
| 6,024,744 A | 2/2000 | Kese et al. |
| 6,033,399 A | 3/2000 | Gines |
| 6,039,733 A | 3/2000 | Buysse et al. |
| 6,050,996 A | 4/2000 | Schmaltz et al. |
| 6,053,914 A | 4/2000 | Eggers et al. |
| D424,694 S | 5/2000 | Tetzlaff et al. |
| D425,201 S | 5/2000 | Tetzlaff et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,273,887 B1 | 8/2001 | Yamauchi et al. |
| 6,277,117 B1 | 8/2001 | Tetzlaff et al. |
| D449,886 S | 10/2001 | Tetzlaff et al. |
| 6,334,861 B1 | 1/2002 | Chandler et al. |
| 6,350,264 B1 | 2/2002 | Hooven |
| 6,352,536 B1 | 3/2002 | Buysse et al. |
| D457,958 S | 5/2002 | Dycus et al. |
| 6,451,018 B1 | 9/2002 | Lands et al. |
| 6,458,130 B1 | 10/2002 | Frazier et al. |
| 6,511,480 B1 | 1/2003 | Tetzlaff et al. |

FOREIGN PATENT DOCUMENTS

| | | | |
|---|---|---|---|
| EP | 0717966 A1 | 6/1996 | |
| EP | 0754437 A3 | 3/1997 | |
| EP | 0853922 A1 | 7/1998 | |
| EP | 0887046 A3 | 1/1999 | |
| EP | 0923907 A1 | 6/1999 | |
| EP | 1034747 A1 | 9/2000 | |
| EP | 1034748 A1 | 9/2000 | |
| EP | 1025807 A3 | 10/2000 | |
| EP | 1034746 A3 | 10/2000 | |
| EP | 1050278 A1 | 11/2000 | |
| EP | 1053719 A1 | 11/2000 | |
| EP | 1053720 A1 | 11/2000 | |
| EP | 1055399 A1 | 11/2000 | |
| EP | 1055400 A1 | 11/2000 | |
| EP | 1080694 A1 | 3/2001 | |
| EP | 1082944 A1 | 3/2001 | |
| GB | 2214430 A | 6/1989 | |
| JP | 5-40112 | 1/1993 | |
| JP | 06343644 A2 | 12/1994 | |
| JP | 07265328 A2 | 10/1995 | |
| JP | 08056955 A2 | 3/1996 | |
| JP | 08252263 A2 | 10/1996 | |
| JP | 09010223 A2 | 1/1997 | |
| JP | 11244298 A2 | 9/1999 | |
| JP | 2000342599 A2 | 12/2000 | |
| JP | 2000350732 A2 | 12/2000 | |
| JP | 2001008944 A2 | 1/2001 | |
| JP | 2001029356 A2 | 2/2001 | |
| JP | 2001128990 A2 | 5/2001 | |
| RU | 401367 | 11/1974 | |
| WO | WO 92/06642 | 4/1992 | |
| WO | WO 95/02369 | 1/1995 | |
| WO | WO 97/00646 | 1/1997 | |
| WO | WO 97/00647 | 1/1997 | |
| WO | WO 97/24073 | 7/1997 | |
| WO | WO 97/24993 | 7/1997 | |
| WO | WO 98/27880 | 7/1998 | |
| WO | WO 99/03407 | 1/1999 | |
| WO | WO 99/03408 | 1/1999 | |
| WO | WO 99/03409 | 1/1999 | |
| WO | WO 99/40857 | 8/1999 | |
| WO | WO 99/51158 | 10/1999 | |
| WO | WO 00/24330 | 5/2000 | |
| WO | WO 00/41638 | 7/2000 | |
| WO | WO 00/53112 | 9/2000 | |

OTHER PUBLICATIONS

Bergadahl et al. "Studies on Coagulation and the Development of an Automatic Computerized Bipolar Coagulator" J. Neurosurg, vol.75, Jul. 1991, pp 148–151.

Kennedy et al. "High–burst–strength, feedback–controlled bipolar vessel sealing" Surgical Endoscopy (1998) 12:876–878.

Peterson et al. "Comparison of Healing Process Following Ligation with Sutures and Bipolar Vessel Sealing" Surgical Technology International (2001).

Linehan et al. "A Phase I Study of the LigaSue Vessel Sealing System in Hepatic Surgery" Section of HPB Surger, Washington University School of Medicine, St. Louis MO, Presented AHPBA, Feb. 2001.

Johnson et al. "Evaluation of the LigaSure Vessel Sealing System in Hemorrthoidectomy" American College of Surgeons (ACS) Clinicla Congress Poster (2000).

Sayfan et al. "Sutureless Closed Hemorrhoidectomy: A New Technique" Annals of Surgery vol.234 No.1 Jul. 2001 pp. 21–24.

Heniford et al. "Initial Results with an Electrothermal Bipolar Vessel Sealer" Surgical Endoscopy (2000) 15:799–801.

Heniford et al. "Initial Research and Clinical Results with an Electrothermal Bipolar Vessel Sealer" 10/99.

McLellan et al. "Vessel Sealing for Hemostasis During Pelvic Surgery" Intl'l Federation of Gynecology and Obstetrics Figo World Congress 2000, Washington, D.C.

Levy et al. "Use of a New Energy–based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10–17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154–157.

Int'l Search Report PCT/US01/11218.

Int'l Search Report PCT/US99/24869.

Int'l Search Report PCT/US98/18640.

Int'l Search Report PCT/US98/23950.

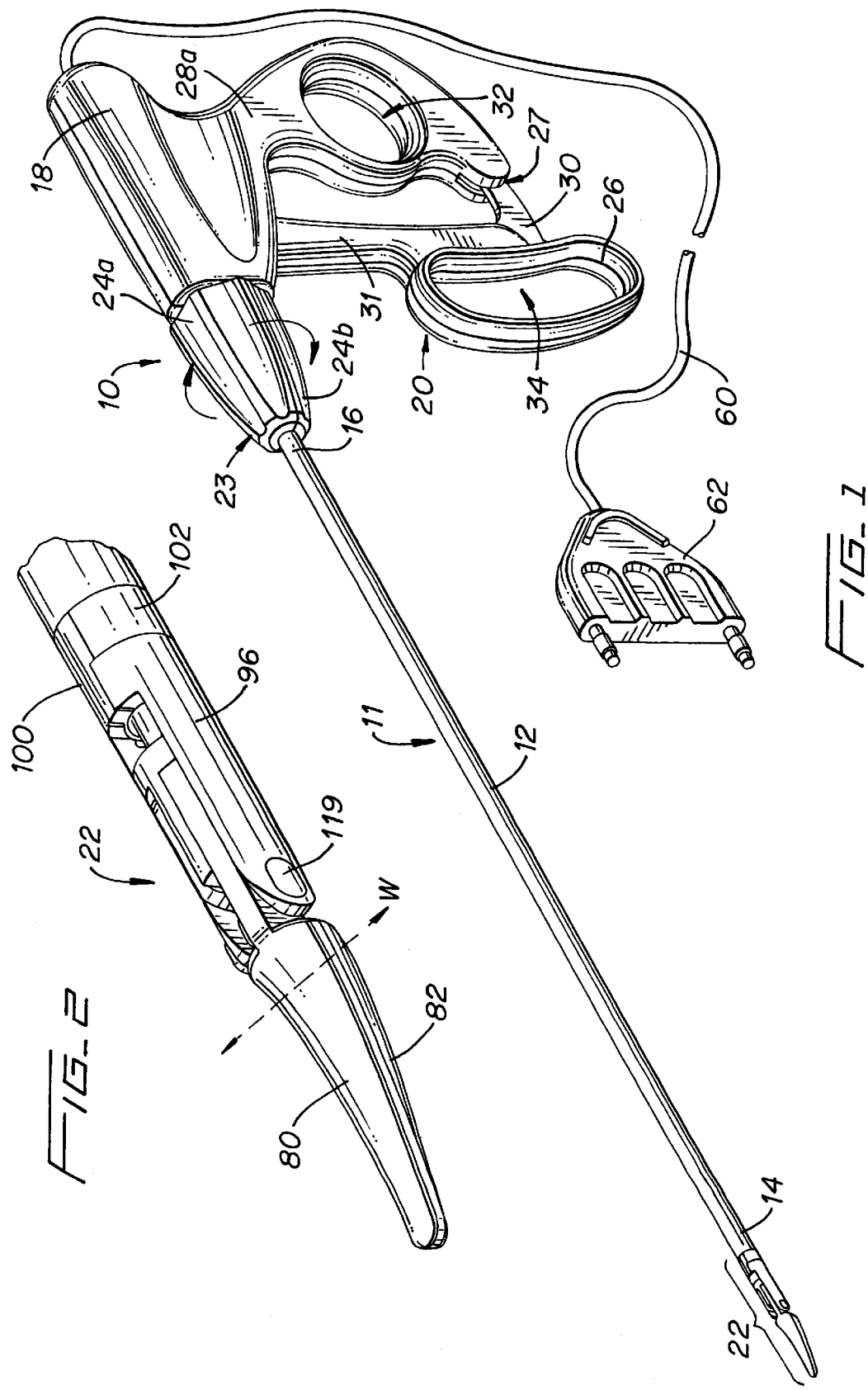

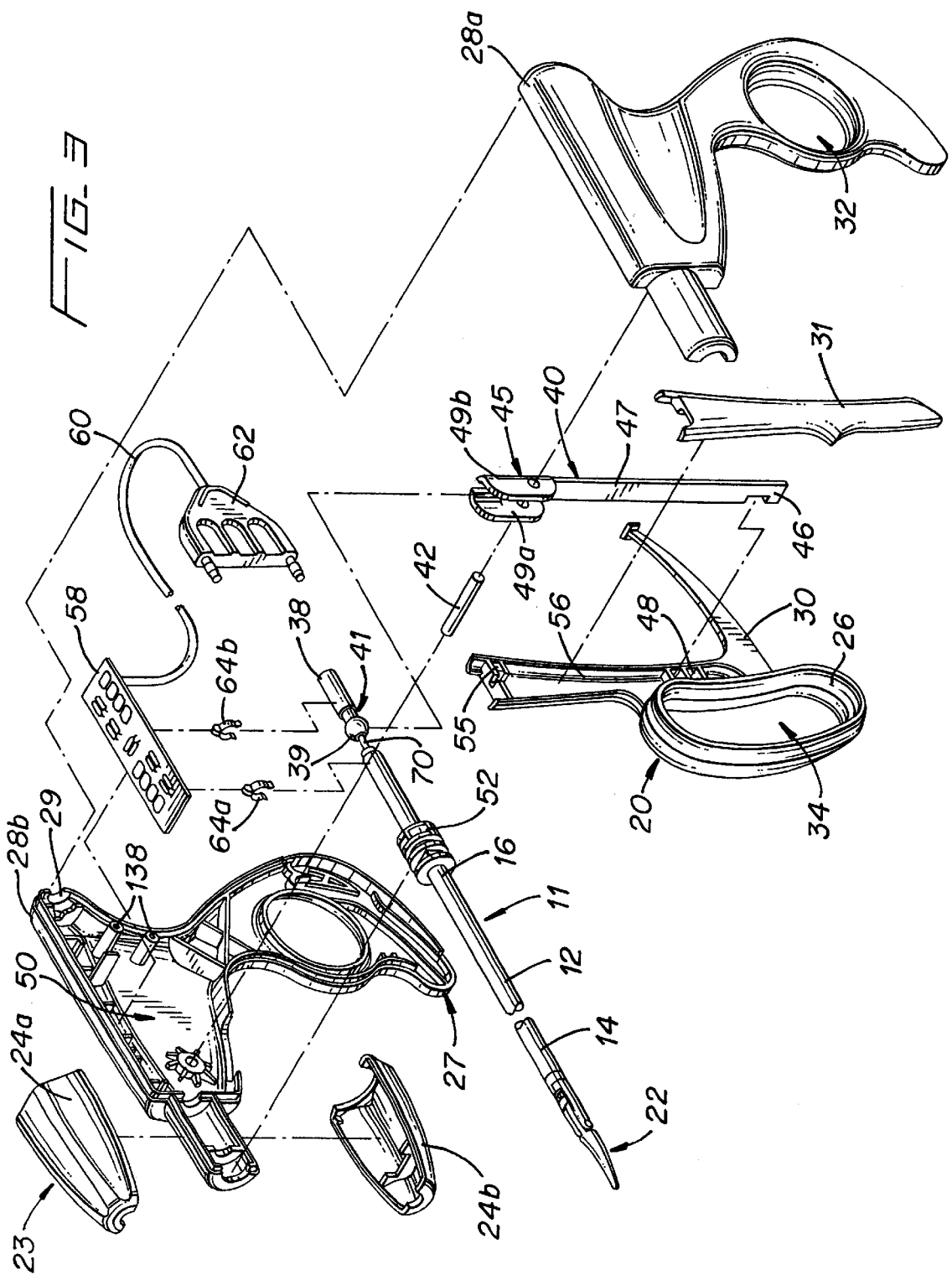

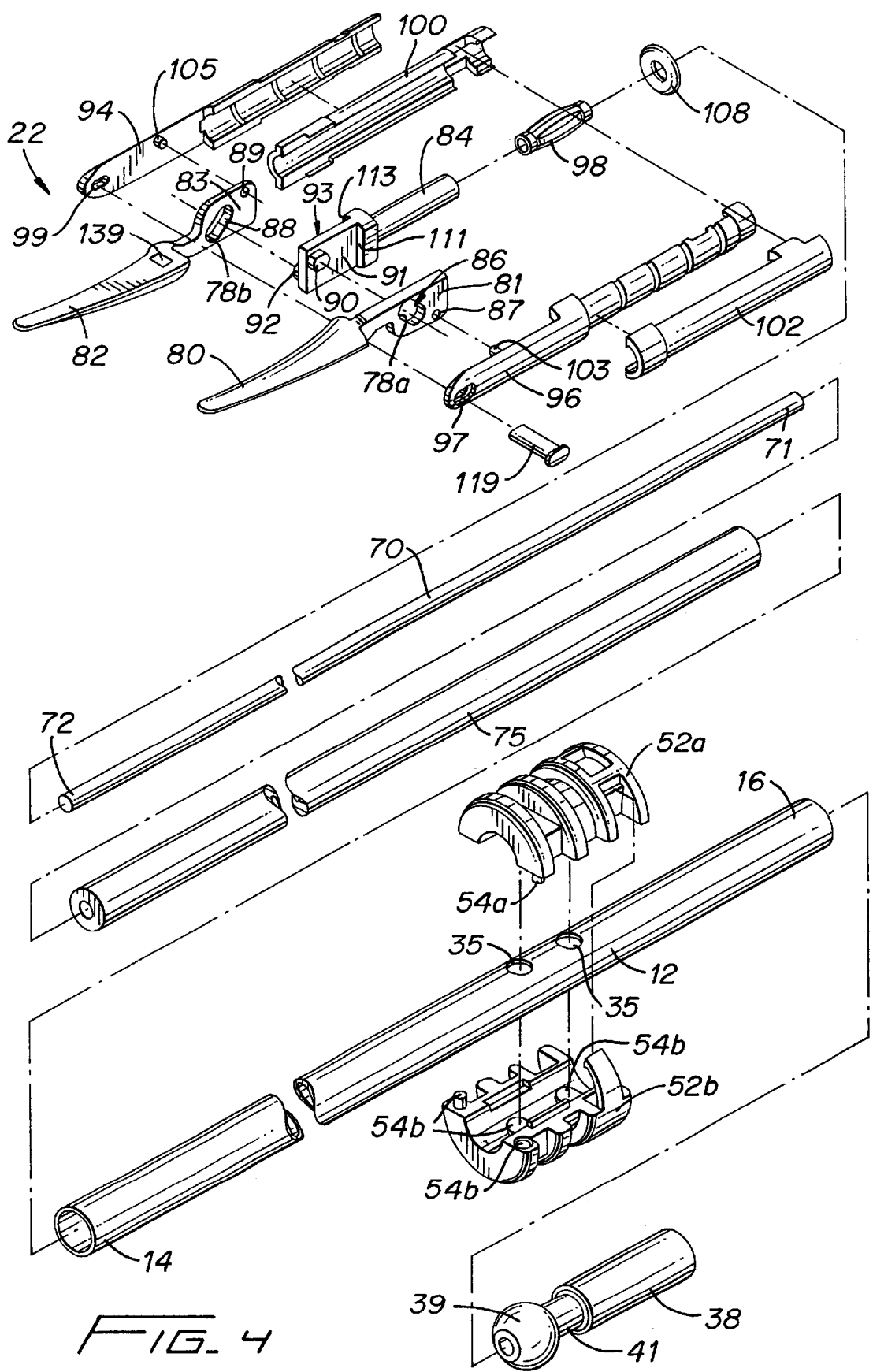

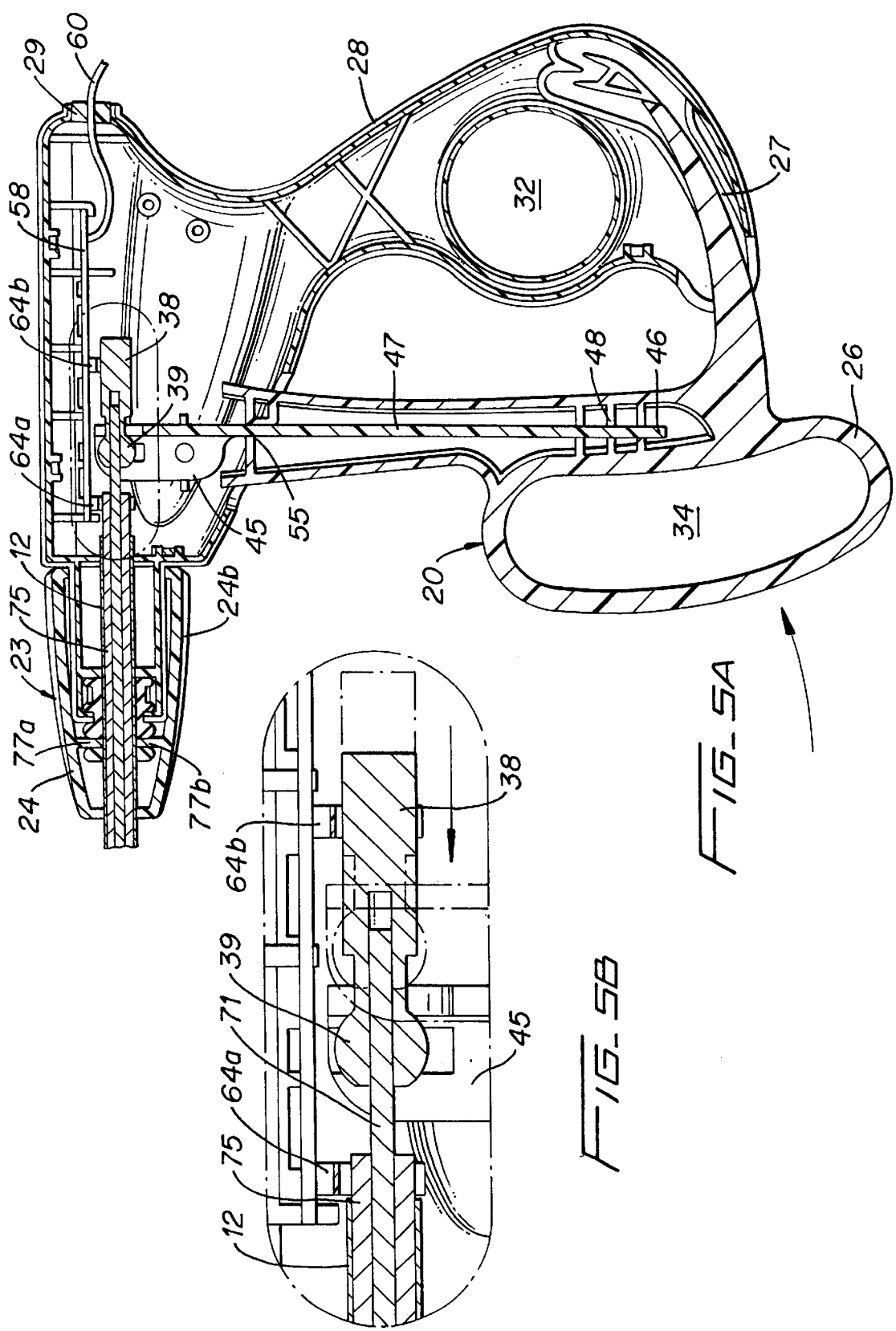

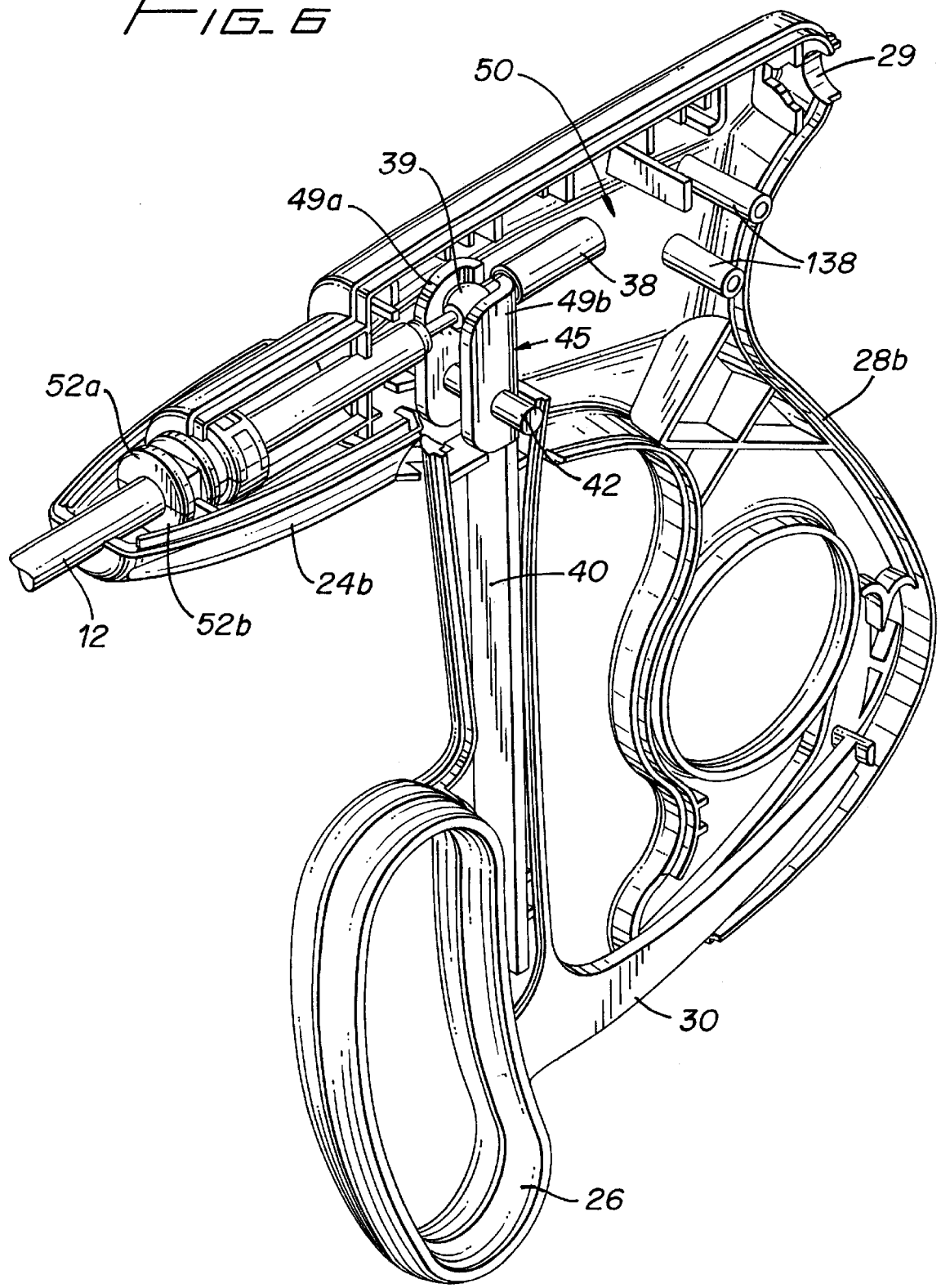

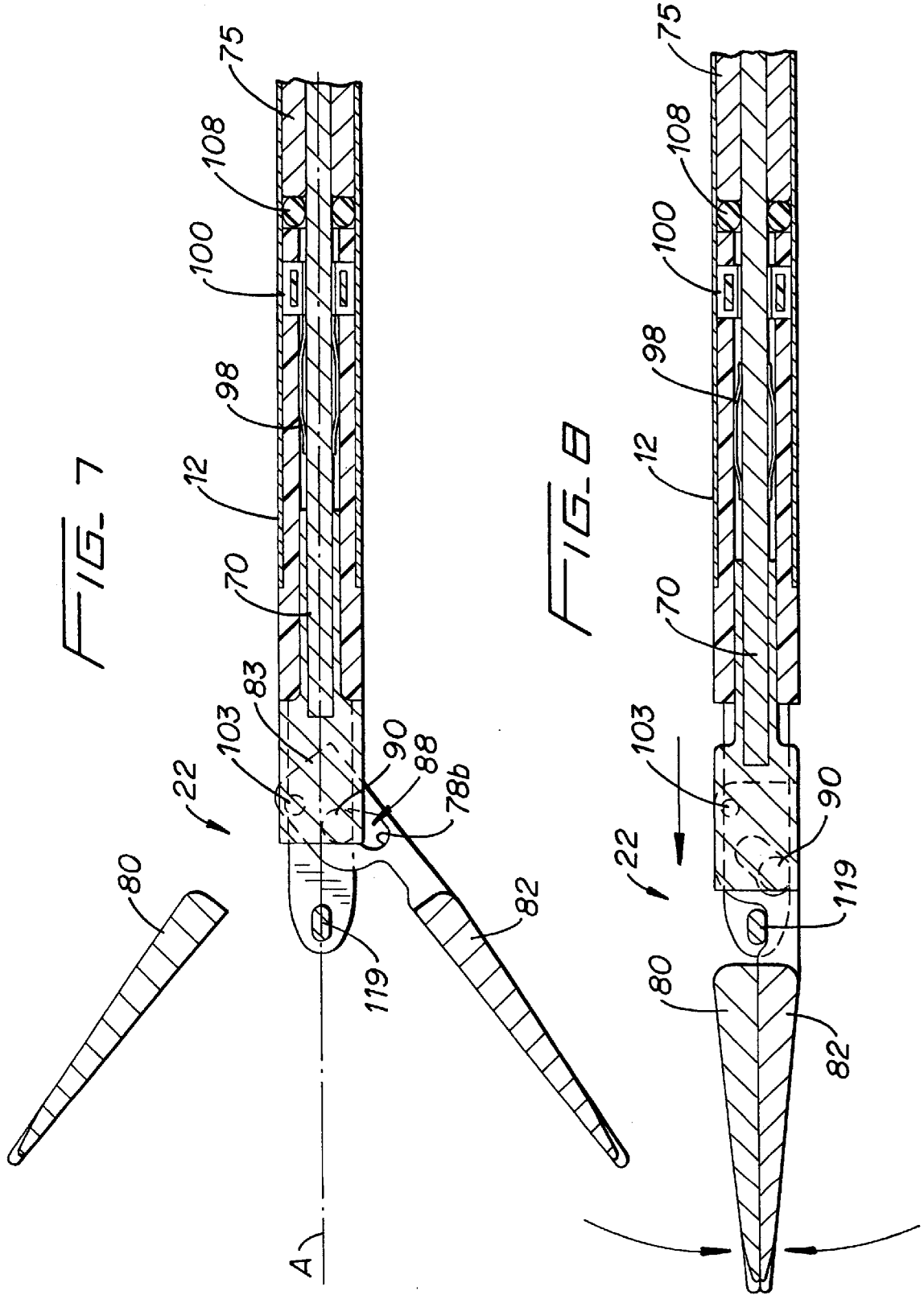

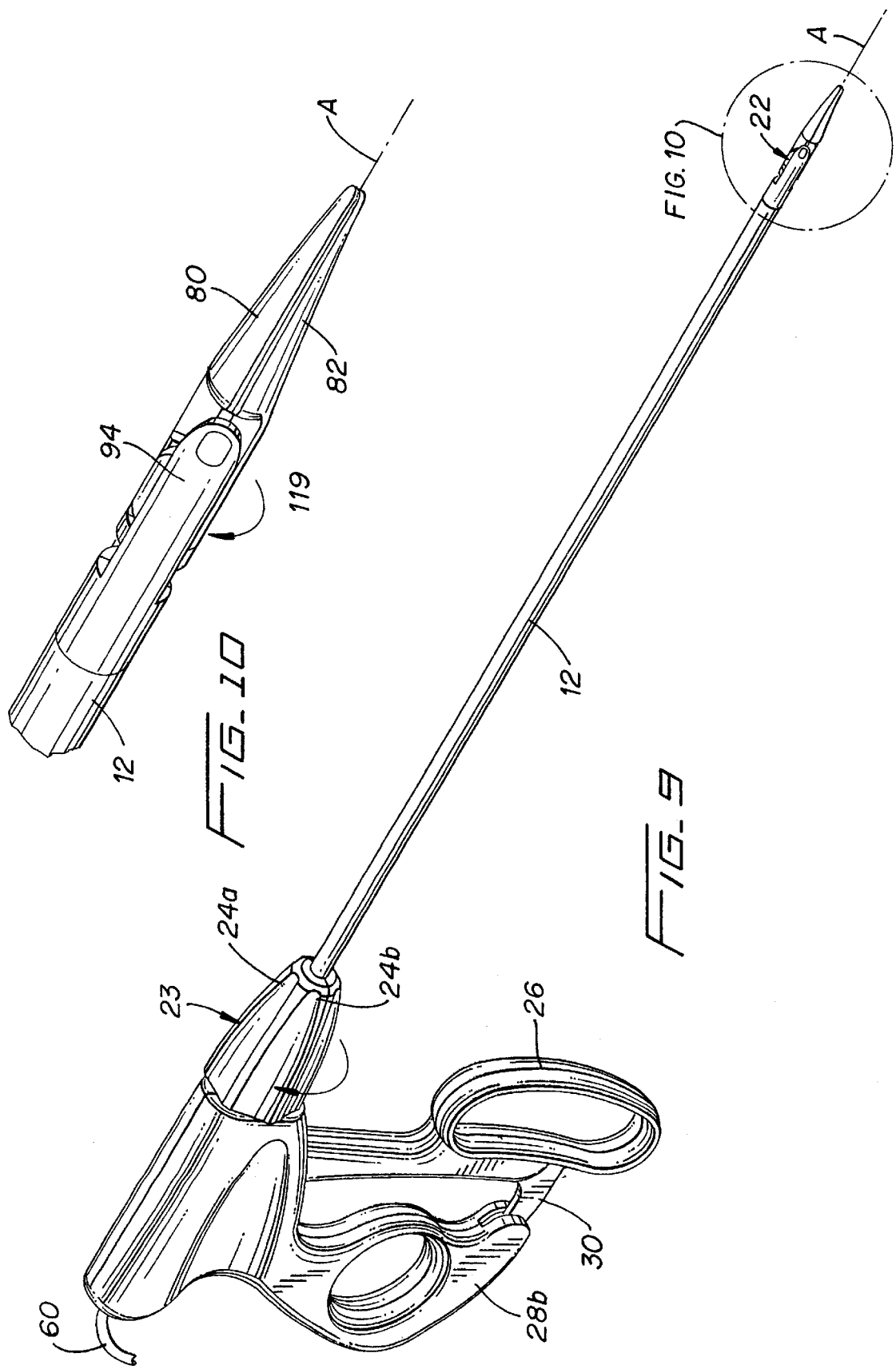

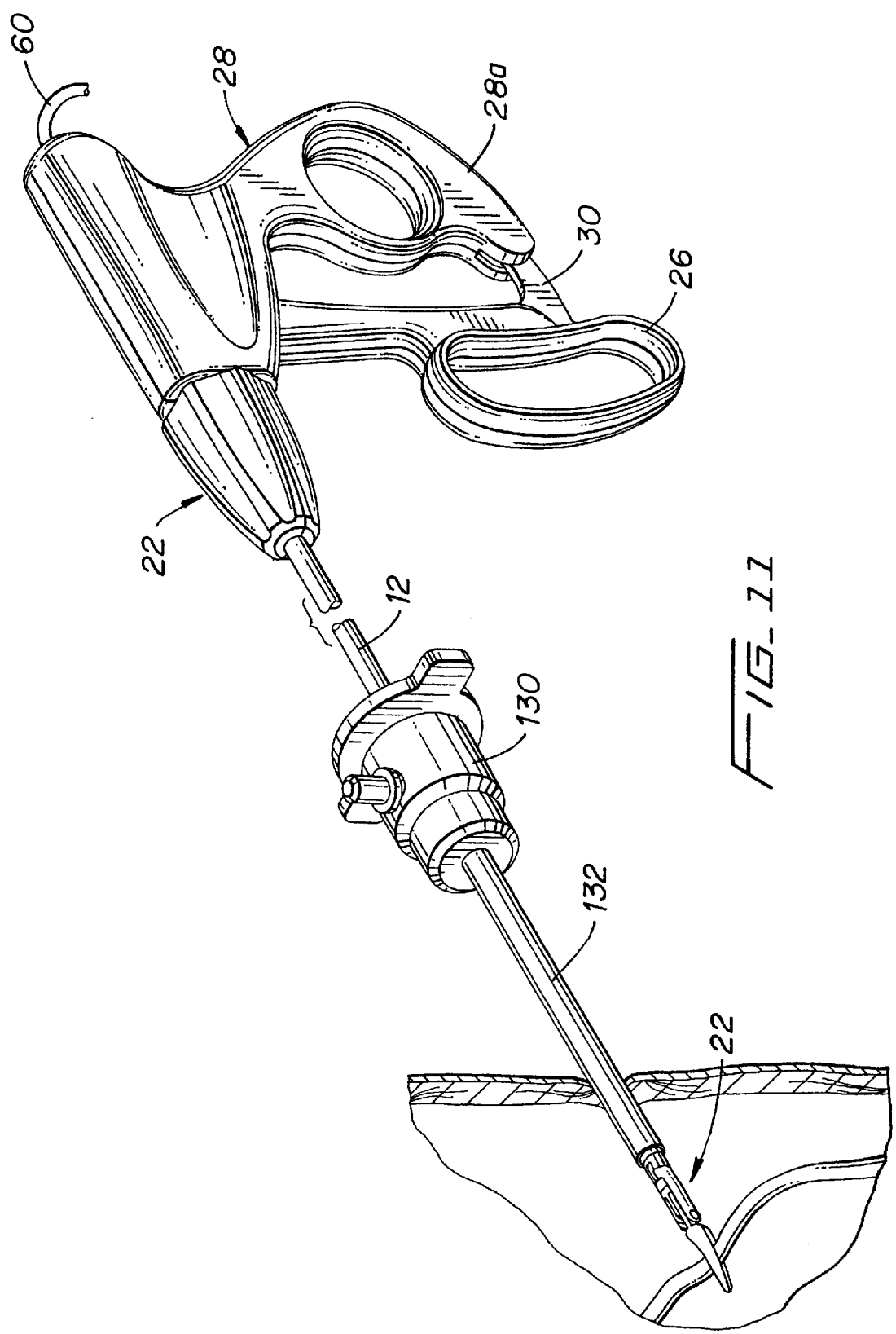
FIG_11

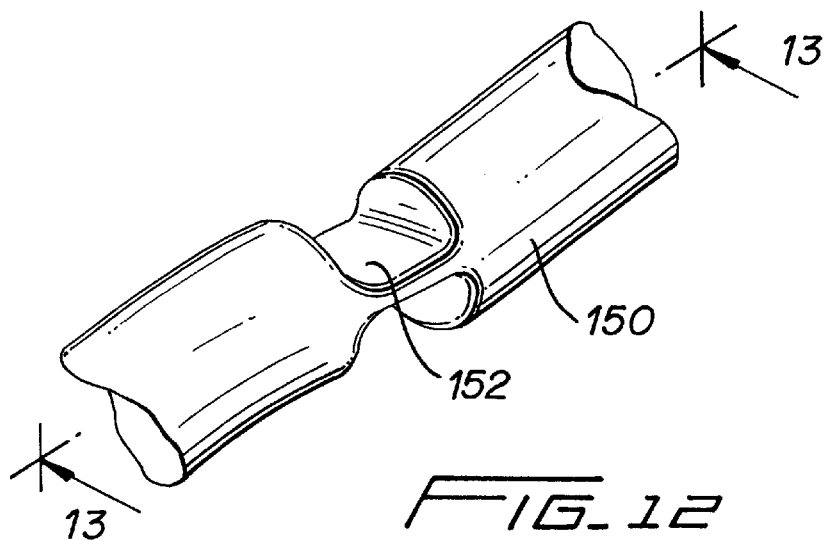
FIG_12
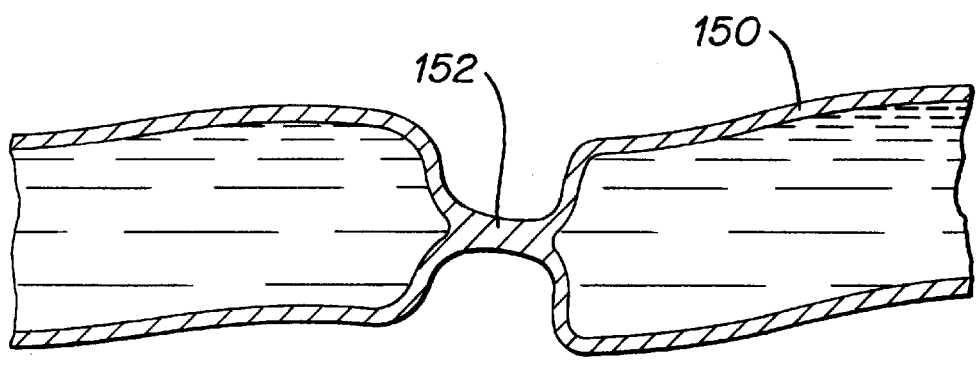
FIG_13
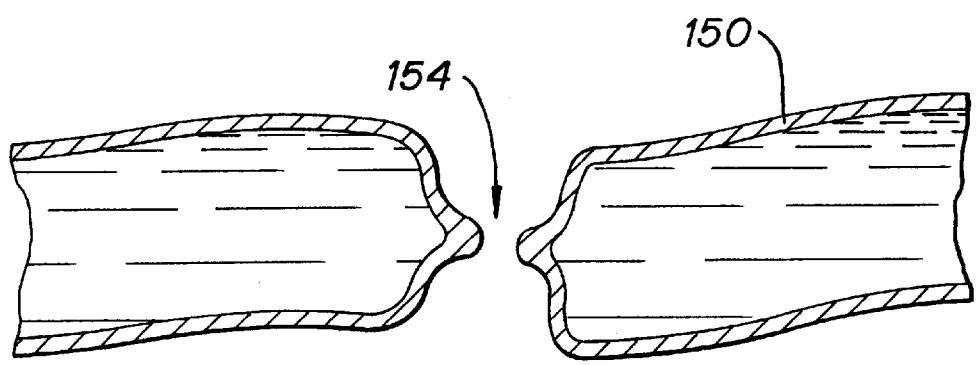
FIG_14

ENDOSCOPIC BIPOLAR ELECTROSURGICAL FORCEPS

This application is a continuation of U.S. application Ser. No. 09/825,500 filed on Apr. 3, 2001, now U. S. Pat. No. 6,458,130, which is a continuation of U.S. application Ser. No. 09/177,950 filed Oct. 23, 1998, now abandoned.

The present disclosure relates to an electrosurgical instrument for performing endoscopic surgical procedures. More particularly, the present disclosure relates to a endoscopic bipolar electrosurgical forceps which utilizes linear displacement of an insulating yoke to grasp and seal tissue between two opposing jaw members.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps are similar clamping devices which utilize both mechanical clamping action and electrical energy to effect hemostasis by heating the tissue and blood vessels to cause coagulation and/or cauterization.

Over the last several decades, more and more surgeons are abandoning traditional open methods of gaining access to vital organs and body cavities in favor of endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, and this presents a design challenge to instrument manufacturers who must find ways to make surgical instruments that fit through the cannulas.

Certain surgical procedures require cutting blood vessels or vascular tissue. However, due to space limitations surgeons can have difficulty suturing vessels or performing other traditional methods of controlling bleeding, e.g., clamping and/or tying-off transected blood vessels. Very small blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187–190, describes a method for terminating electrosurgical power to the vessel so that charring of the vessel walls can be avoided.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

Several bipolar endoscopic instruments are known. For example: U.S. Pat. No. 3,938,527 discloses a bipolar endoscopic instrument for tubal cauterization; U.S. Pat. No. 5,250,047 discloses a bipolar endoscopic instrument with a replaceable electrode tip assembly; U.S. Pat. No. 5,445,638 discloses a bipolar coagulation and cutting forceps with first and second conductors extending from the distal end; U.S. Pat. No. 5,391,166 discloses a bipolar endoscopic instrument having a detachable working end; and U.S. Pat. No. 5,342,359 discloses a bipolar coagulation device.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, coagulation is defined as a process of desiccating tissue wherein the tissue cells are ruptured and dried and vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. No. 4,005,714 to Hiltebrandt, U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al., all relate to electrosurgical instruments for coagulating, cutting and/or sealing vessels or tissue.

These instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. It is also undesirable to increase the moment arm of the pins because the physical size of the jaw members and other component parts might not fit through a cannula.

Thus, a need exists to develop a bipolar forceps which effectively seals vascular tissue and solves the problem of providing a large closure force between the opposing jaws members using a compact design that is capable of fitting through a cannula without risking structural failure of the instrument yoke.

SUMMARY

The present disclosure relates to a endoscopic bipolar forceps for clamping and sealing tissue which includes first and second jaw members pivotally attached in opposing relation relative to one another which are movable from a first open position wherein the jaw members are disposed in spaced relation relative to one another to a second clamping position wherein the jaw members cooperate to grasp tissue therebetween. A drive rod assembly connects each of the jaw members to a source of electrical energy such that the jaw members are capable of conducting bipolar energy through the tissue held therebetween. A handle is attached to the drive rod assembly and imparts movement of the first and second jaw members from the first and second positions. At least one stop member preferably made from an insulating material is attached to the jaw members for controlling the distance between the jaw members.

Preferably, the handle includes an actuator having a lost motion connection between the jaw members and the actuator for transferring user manipulation of the actuator to the jaw members so as to maintain a predetermined or maximum clamping force within a preferred range irrespective of the user manipulation during sealing of the tissue between the jaw members.

In one embodiment, the forceps includes a rotating assembly for controlling the rotational movement of the jaw members. In another embodiment, the jaw members and the drive assembly are connected by a cam follower mechanical linkage for imparting movement of the jaw members relative to one another.

Another embodiment of the present disclosure includes a bipolar forceps having first and second jaw members pivotally attached in opposing relation relative to one another, the jaw members being movable from a first open position wherein the jaw members are disposed in spaced relation relative to one another to a second clamping position wherein the jaw members cooperate to grasp tissue therebetween. A drive rod assembly connects each of the jaw members to a source of electrical energy such that the jaw members are capable of conducting bipolar energy through the tissue held therebetween. A yoke member is attached to the distal end of the drive rod assembly and between the jaw members. Preferably, a handle is attached to the drive rod assembly and imparts linear movement to the yoke member which, in turn, imparts movement of the two opposing jaw members relative to one another by virtue of a cam-follower mechanical linkage.

Preferably, each jaw member includes a flange which extends therefrom and the yoke includes a pair of shoulder portions which are dimensioned to abut the flanges when the jaw members are moved into the second position. The shoulder portions relieve shear stresses on the cam-follower linkage during clamping and sealing of the tissue.

In another embodiment, each of the jaw members includes a cam slot located therethrough and the yoke includes at least one corresponding detent which engages the cam slots such that movement of the yoke imparts movement of the jaw members relative to one another. Preferably, each of the cam slots includes a cul-de-sac positioned therein to relieve shear stress on the detent approximately when the shoulder portions of the yoke member engage the flanges of the jaw members. Preferably, the inner periphery of the cam slots are shaped to impart at least two different movements to the jaw members relative to one another.

BRIEF DESCRIPTION OF THE DRAWINGS

FIG. 1 is a perspective view of a forceps according to the present disclosure;

FIG. 2 is an enlarged, perspective view of an end effector assembly of the forceps of FIG. 1;

FIG. 3 is a perspective view with parts separated of a handle assembly and activator of the forceps of FIG. 1;

FIG. 4 is an enlarged, perspective view with parts separated of the end effector assembly and a drive rod assembly of the forceps of FIG. 1;

FIG. 5A is a side, partial cross-section of the handle assembly and drive rod assembly of the forceps of FIG. 1;

FIG. 5B is an enlarged, side cross-section of the indicated area of detail shown in FIG. 5A;

FIG. 6 is a perspective view of the handle assembly, activator and drive rod assembly of the forceps of FIG. 1;

FIG. 7 is an enlarged, partial cross-section of the end effector assembly shown with a pair of jaw members in the open configuration;

FIG. 8 is an enlarged, partial cross-section showing the linear motion of the drive rod assembly against a cam follower of the end effector assembly to effect closure of the jaw members;

FIG. 9 is a perspective view of the forceps showing the rotational movement of a rotating assembly which rotates the end effector assembly about a longitudinal axis "A";

FIG. 10 is an enlarged perspective view of the indicated area of detail shown in FIG. 9;

FIG. 11 is a perspective view of the forceps of the present disclosure shown sealing a tubular vessel through a cannula assembly;

FIG. 12 is an enlarged perspective view of a sealing site of a tubular vessel;

FIG. 13 is a longitudinal cross-section of the sealing site taken along line 13—13 of FIG. 12; and FIG. 14 is a longitudinal cross-section of the sealing site of FIG. 12 after separation of the tubular vessel.

DETAILED DESCRIPTION OF THE PREFERRED EMBODIMENTS

Referring now to FIGS. 1–3, a bipolar forceps 10 for use with endoscopic surgical procedures includes a drive rod assembly 11 which is coupled to a handle assembly 18. The drive rod assembly 11 includes an elongated hollow shaft portion 12 having a proximal end 16 and a distal end 14. In the drawings and in the descriptions which follow, the term "proximal", as is traditional, will refer to the end of the bipolar forceps 10 which is closer to the user, while the term "distal" will refer to the end which is further from the user.

An end effector assembly 22 is attached to the distal end 14 of shaft 12 and includes a pair of opposing jaw members 80 and 82. Preferably, handle assembly 18 is attached to the proximal end 16 of shaft 12 and includes an activator 20 for imparting movement of the jaw members 80 and 82 from an open position wherein the jaw members 80 and 82 are disposed in spaced relation relative to one another, to a clamping or closed position wherein the jaw members 80 and 82 cooperate to grasp tissue 150 therebetween.

As best seen in FIG. 3, activator 20 includes a movable handle 26 having an aperture 34 defined therein for receiving at least one of the operator's fingers and a fixed handle 28 having an aperture 32 defined therein for receiving an operator's thumb. Movable handle 26 is selectively moveable from a first position relative to fixed handle 28 to a second position in closer proximity to the fixed handle 28 to close jaw members 80 and 82. Preferably, fixed handle 28 includes a channel 27 which extends proximally for receiving a ratchet 30 which is coupled to movable handle 26. This structure allows for progressive closure of end effector assembly 22 as well as locking engagement of opposing jaw members 80 and 82. In some cases it may be preferable to include other mechanisms to control and/or limit the movement of handle 26 relative to handle 28 such as, e.g., hydraulic, semi-hydraulic and/or gearing systems.

Fixed handle 28 includes a rotating assembly 23 for controlling the rotational movement of end effector assembly 22 about a longitudinal axis "A" of the elongated shaft 12 (see FIGS. 9 and 10). Preferably, rotating assembly 23 includes upper and lower knob portions 24a and 24b, respectively, which releasably engage one another about a gear 52 which is attached to shaft 12. Preferably, the ratio of rotation of rotating assembly 23 to end effector assembly 22 is 1:1, however, it is contemplated that a different gearing structure may be incorporated to increase or decrease the rotational ratio depending upon a particular purpose.

Preferably, a pair of handle sections 28a and 28b engage one another by way of a plurality of mechanical interfaces to form fixed handle 28. The mechanical interfaces include sockets 138 which are formed in handle section 28b and which are dimensioned to receive a complimentary plurality of detents (not shown) attached to handle section 28a. While the term socket is used herein, it is contemplated that either a male or female mechanical interface may be used on either handle section with a mating mechanical interface disposed on the opposite handle section.

As best seen in FIG. 3, each handle section 28a and 28b is generally hollow such that a cavity 50 is formed therein for housing various internal components which make up the forceps 10. For example, cavity 50 houses a PC board 58 which controls the electrosurgical energy being transmitted from an electrosurgical generator (not shown) to each jaw member 80 and 82. More particularly, electrosurgical energy is generated from an electrosurgical generator and transmitted to the PC board by cable 60 which attached through a wire port 29 disposed in the proximal end of handle assembly 18. The PC board 58 converts the electrosurgical energy from the generator into two different electrical potentials which are transmitted to each jaw member 80 and 82 by a separate terminal clip 64b and 64a, respectively, which will be explained in more detail below with respect to FIG. 4.

Preferably, a lost motion mechanism is positioned between each of the handle sections 28a and 28b for maintaining a predetermined or maximum clamping force for sealing tissue between the jaw members 80 and 82. In the particular embodiment shown in FIG. 3, the lost motion mechanism comprises a resilient arm 40 which is connected between handle sections 28a and 28b by pin 42. More particularly, the arm includes a lower end 46, an upper end 45 and shaft portion 47 located therebetween. Preferably, upper end 45 is bifurcated forming a clevis having upwardly extending flanges 49a and 49b, respectively, and the lower end 46 is dimensioned to engage a step-like interface 48 located on movable handle portion 26. The shaft portion 47 is secured within an elongated channel 56 formed within movable handle portion 26. Preferably, a cover plate 31 attaches to movable handle 26 by conventional means such as snap-fit engagement to further secure arm 40 within handle 26.

Referring to FIG. 4, rod assembly 11 includes a drive rod 70 which has a proximal end 71 and a distal end 72. A piston 38 is attached to the proximal end 71 of drive rod 70 and includes a generally rounded head portion 39 and a notch 41 located between the head portion 39 and the proximal end of piston 38. Preferably, clevis flanges 49a and 49b of arm 40 are dimensioned to receive head 39 therebetween when arm 40 is assembled between handle sections 28a and 28b (see FIG. 6). Movement of the handle 26 towards fixed handle 28 imparts pivotal movement of the upper end 45 of arm 40 at a pivot point 55 (see FIG. 5A) which, in turn, imparts movement of the piston 38 from a first position wherein the piston 38 is disposed further from end effector assembly 22 to a second position wherein piston 38 is in closer proximity to end effector assembly 22 (see FIG. 5B). As explained in greater detail below, movement of the piston 38 between first and second positions imparts linear movement to drive rod 70 which, in turn, moves jaw members 80 and 82 toward and away from each other.

Seating the generally rounded head 39 between clevis flanges 49a and 49b enables the user to utilize the rotating assembly 23 effectively without interfering with the linear movement of the piston 38.

As best seen in the exploded view of FIG. 4, the end effector assembly 22 includes first jaw 80, second jaw 82 and an electrically insulating yoke 84 disposed therebetween. Preferably, jaw member 80 and jaw member 82 are movable from an open position to a closed position by movement of the handle assembly 18 as described above. It is contemplated that either both or one of the jaw members 80 and 82 can be movable relative to one another. First jaw member 80 has a first flange 81 which extends therefrom and a cam slot 86 located therethrough. Likewise, second jaw 82 has a second flange 83 which extends therefrom and a cam slot 88 located therethrough. Preferably, each jaw 80 and 82 is formed from a stainless steel or some other electrically conductive material.

The end effector assembly 22 also includes an outer nose portion 94 and an inner nose portion 96 which engage jaw members 82 and 80, respectively. A first pivot 105 is located on outer nose portion 94 and is dimensioned to engage a corresponding pivot hole 89 located on flange 83. A second pivot 103 is located on inner nose portion 96 and is dimensioned to engage a corresponding pivot hole 87 located on flange 81. The center of rotation for first jaw member 80 is at a first pivot hole 87 and the center of rotation for second jaw member 82 is at a second pivot hole 89. Preferably, each nose portion 94 and 96 is made from an electrically conductive material and transmits electrosurgical energy to a respective jaw member 82 and 80 as described in more detail below.

As mentioned above with respect to FIG. 3, electrosurgical energy is transmitted from the electrosurgical generator to the PC board 58 which converts the energy into first and second poles. A pair of terminal clips 64a and 64b are connected to PC board 58 and transfer the first and second poles of alternating potential, respectively, to the drive rod assembly 11. Clip 64a connects to shaft 12 and conducts the first pole to jaw member 82 and clip 64b connects to piston 38 which is, in turn, connected to drive rod 70. The second pole is conducted along drive rod 70 to jaw member 80. Both the drive rod 70 and the shaft 12 are made from an electrically conductive material and preferably an insulation sleeve 75 is disposed between drive rod 70 and shaft 12 to prevent the forceps 10 from short circuiting.

As best seen in FIG. 4, the inner nose portion 96 is electrically connected with drive rod 70 and the outer nose portion 94 is electrically connected to shaft 12. The inner and outer nose portions 96 and 94 capture yoke 84 along with flanges 83 and 81. Yoke 84 moves axially along axis "A" (see FIGS. 7 and 8) in a space between inner and outer portions 96 and 94 and a spacer stake 119 maintains the separation of the nose portions 96 and 94 at their distal ends. Stake 119 is dimensioned to engage and lock the inner and outer nose portions 96 and 94 together, which, in turn locks jaw member 80 and 82 atop yoke 84. In some cases it may be preferable to dimension stake 119 such that stake 119 acts as a stop member and controls the gap distance between the opposing jaw members 80 and 82 relative to one another. In this case, stake 119 is formed from an electrically insulative material such as plastic. The nose portions 94 and 96 provide lateral support for the flanges 81 and 83 and help ensure that detents 90 and 92 remain within cam slots 86 and 88, respectively.

End effector assembly 22 also includes an inner insulator 102 and an outer insulator 100 for maintaining electrical insulation between poles. Outer insulator 100 insulates outer nose portion 94 from inner nose portion 96 and drive rod 70 which conduct the second pole of electrical energy. Inner insulator 102 insulates inner nose portion 96 from outer nose portion 94 and shaft 12 which conduct the first pole of electrical energy. In this manner, outer nose portion 94 can provide electrical continuity between shaft 12 and jaw member 82, while inner nose portion 96 can provide electrical continuity between drive rod 70 and jaw member 80.

Preferably, a spring contact 98 is utilized to maintain the electrical connection between drive rod 70 and inner nose portion 96 during axial motion of the drive rod 70. A donut-shaped spacer 108 can also be utilized to assure linear motion of the drive rod 70 within sleeve 75 and to prevent accidental short circuiting of the forceps 10.

As mentioned above and as best seen in FIG. 4, rod assembly 11 also includes gear 52 which attaches to shaft 12 which facilitates rotational movement of the end effector assembly 22 about axis "A". More particularly, gear 52 includes an upper portion 52a and a lower portion 52b which each have a pair of outwardly extending mechanical interfaces 54a and 54b, respectively, which are dimensioned to releasably engage a corresponding pair of mechanical interfaces 35 disposed through shaft 12. Preferably, gear 52 is made from an electrically insulative material such as, e.g., plastic, to avoid transferring electrosurgical energy to the rotating assembly 23. As best seen in FIG. 5A, rotating assembly 23 includes two half sections 24a and 24b which each include a flange 77a and 77b, respectively, which extends outwardly therefrom for engaging gear 52. Rotation of assembly 23 effects rotational movement of the shaft 12 which, in turn, rotates the end effector assembly 22 about axis "A" (see FIGS. 9 and 10).

Referring back to FIG. 4, yoke 84 is preferably formed from an electrically insulative material such as plastic. A first side 91 of yoke 84 faces first flange 81 and a second side 93 of yoke 84 faces second flange 83. When yoke 84 is positioned between flanges 81 and 83, yoke 84 electrically insulates first jaw member 80 from second jaw member 82. In this manner, bipolar electrosurgical current can be conducted through tissue 150 which is grasped between jaws 80 and 82 without flanges 81 and 83 short circuiting.

Yoke 84 also includes first detent 90 located on the first side 91 which is dimensioned to movably engage cam slot 86 and a second detent 92 located on the second side 93 which is dimensioned to engage cam slot 88. Preferably, the detent and cam slot combination, 90, 86 and 92, 88, respectively, work together as a cam-follower mechanical linkage. Linear motion of drive rod 70 along axis "A" moves the yoke 84 causing detent 90 and 92 to slide within their respective cam slots 86 and 88. In one embodiment, slots 86 and 88 are angled with respect to the distal ends of the jaws 80 and 82 such that the jaws 80 and 82 move in a generally arcuate fashion toward and away from each other.

In another embodiment, the inner periphery of the cam slots 86 and 88 are shaped to include two angles which, in turn, cause the jaw members 80 and 82 to move in two separate and distinct fashions relative to one another upon movement of drive rod 70. For example, cam slots 86 and 88 can include a first or proximal stage which effects generally arcuate movement of the jaw members 80 and 82 relative to one another and a second or distal stage wherein the jaw members 80 and 82 move in a more linear fashion relative to one another. It is envisioned that the cam slots 86 and 88 can be dimensioned to effect other movements of the jaw members 80 and 82 relative to one another depending upon a particular purpose, e.g., parabolic movement, cycloidal movement, and/or sinusoidal movement.

As seen best with respect to FIGS. 7 and 8, detents 90 and 92 provide a force against the corresponding inner periphery of cam slots 86 and 88 creating a moment about pivots 103 and 105, respectively. Preferably, cam slots 86 and 88 are arranged such that distal motion of the drive rod 70 causes the jaw members 80 and 82 to move together. Once the jaw members 80 and 82 are closed together, it is envisioned that jaws 80 and 82 are held in clamped positioned by a continued compressive force on the rod 70 due to handle member 26. As mentioned above, the handle assembly 18 can include a lost motion mechanism for maintaining a predetermined or maximum clamping force for sealing tissue 150 between the jaw members 80 and 82

One of the advantages of the present disclosure is that excessive clamping forces which are normally associated with detents 90 and 92 are offloaded by the unique configuration of yoke 84 which prevents mechanical failure of the forceps 10. More particularly, the cam slots 86 and 88 are preferably dimensioned such that the cam-follower motion of the detents 90 and 92 within cam slots 86 and 88 simply operate to clamp the tissue 150 between the jaw members 80 and 82 and a small moment arm is created between the detents 90 and 92 and pivots 103 and 105, respectively. Before the detents 90 and 92 reach their distal most positions within the cam slots 86 and 88, respectively, a pair of shoulders 111 and 113 located on the yoke 84 are dimensioned to engage flanges 81 and 83 and offload any additional clamping force applied by the handle assembly 18.

In some cases it may be preferable to dimension cam slots 86 and 88 to have an enlarged distal end or cul-de-sac 78a and 78b such that the cam-follower motion of detents 90 and 92 at their distal most point within slots 86 and 88 will come to rest within the cul-de-sac 78a and 78b allowing the closure force to be offloaded by shoulders 111 and 113 abutting flanges 81 and 83. It is envisioned that the cul-de-sacs 78a and 78b which are positioned within cam slots 86 and 88 will relieve shear stress on the detents 90 and 92 approximately at the same time when the shoulder portions 111 and 113 of the yoke 84 engage the flanges 81 and 83 to provide a closure force between the jaw members 80 and 82.

The shoulders 111 and 113 abut the proximal end of flanges 81 and 83 to cause jaw members 80 and 82 to close together with greater closure force. In other words, shoulder portions 111 and 113 provide a relatively large moment about pivots 103 and 105 to effect a high closure force between the jaw members 80 and 82. The unique configuration of the cam-follower linkage together with the shoulders 111 and 113 offloading high clamping forces prevent detents 90 and 92 from breaking due to mechanical failure. Since the pivots 103 and 105 are preferably made of metal and can withstand relatively high shear forces, the yoke 84 and its component parts can be formed from an inexpensive insulating material such as plastic without risk of mechanical failure due to the high clamping forces necessary to seal tissue. As mentioned above, forming the yoke 84 from insulative materials will also prevent the jaw members 80 and 82 from shorting.

Two mechanical factors play an important role in determining the resulting thickness of the sealed tissue and effectiveness of the seal, i.e., the pressure applied between opposing jaw members 80 and 82 and the gap between the opposing jaw members 80 and 82 during the sealing process. However, thickness of the resulting tissue seal cannot be adequately controlled by force alone, i.e., too much force and the two jaw members 80 and 82 would touch and little energy would travel through the tissue resulting in a bad seal or too little force and the seal would be too thick. Applying the correct force is important for other reasons: to oppose the walls of the vessel; reduce the tissue impedance to a low enough value that allows enough current through the tissue; and to overcome the forces of expansion during tissue heating in addition to contributing towards creating the required end tissue thickness which is an indication of a good seal.

As best seen in FIG. 4, in order to achieve a desired gap range (e.g., about 0.001 to about 0.006 inches) and apply a desired force to seal the tissue, at least one jaw member 80 and/or 82 includes a stop member 139 which limits the movement of the two opposing jaw members 80 and 82 relative to one another. As explained above, in some cases it may be preferable to dimension stake 119 such that it acts like a stop member and limits the movement of the two opposing jaw members 80 and 82 relative to one another. Preferably, stop member 139 and/or stake 119 is made from an insulative material and is dimensioned to limit opposing movement of the jaw members 80 and 82 to within the above gap range.

The seal surfaces of the jaw members 80 and 82 are relatively flat to avoid current concentrations at sharp edges and to avoid arcing between high points. In addition and due to the reaction force of the tissue 150 when engaged, jaw members 80 and 82 are preferably manufactured to resist bending. For example and as best seen in FIG. 2, the jaw members 80 and 82 are preferably tapered along width "W" which is advantageous for two reasons: 1) the taper will apply constant pressure for a constant tissue thickness at parallel; 2) the thicker proximal portion of the jaw members 80 and 82 will resist bending due to the reaction force of the tissue 150.

FIG. 11 shows the bipolar forceps 10 during use wherein movement of the handle assembly applies clamping force on the tubular tissue 150 to effect a seal 152 as shown in FIGS. 12 and 13. More particularly, shaft 12 and end effector assembly 22 are inserted through a trocar 130 and cannula 132 and handle 26 is moved progressively towards fixed handle 28 to cause jaw members 80 and 82 to grasp tubular vessel 150 therebetween. After the jaw members 80 and 82 are closed about the tissue 150, the user then applies electrosurgical energy to the tissue 150. By controlling the intensity, frequency and duration of the electrosurgical energy applied to the tissue 150, the user can either cauterize, coagulate/desiccate seal and/or cut tissue and/or simply reduce or slow bleeding. As shown in FIGS. 13 and 14, once the tubular vessel is sealed, the vessel 150 can be cut along seal 152 to separate the tissue 150 and form gap 154 therebetween.

From the foregoing and with reference to the various figure drawings, those skilled in the art will appreciate that certain modifications can also be made to the present disclosure without departing from the scope of the present disclosure. For example, it may be preferable to add other features to the forceps 10, e.g., an articulating assembly to axially displace the end effector assembly 22 relative to the elongated shaft 22.

While only one embodiment of the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A bipolar endoscopic instrument for sealing tissue, comprising:

a pair of first and second jaw members having opposite electrical potentials and being movable from a first position in spaced relation relative to one another to a second position wherein the jaw members cooperate to conduct bipolar energy through tissue held therebetween, each jaw member including a tissue sealing surface;

a yoke which electrically insulates the jaw members during activation and sealing, the yoke including:
at least one detent which moves the jaw members from the first to second positions upon linear reciprocation of the yoke;
a pair of shoulder portions which abut the jaw members in the second position and offload pressure on the pin during clamping and sealing of tissue; and at least one stop member attached to at least one of the tissue sealing surfaces of one of the jaw members for controlling the distance between opposing jaw members during sealing.

2. A bipolar endoscopic instrument for sealing tissue, comprising:

a handle;

an elongated drive rod having distal and proximal ends;

a pair of first and second jaw members being disposed in electro-mechanical communication with the elongated drive rod and being movable upon reciprocation of the elongated drive rod from a first position wherein the jaw members are disposed in spaced relation relative to one another to a second position wherein the jaw members cooperate to conduct bipolar energy through tissue held therebetween;

a resilient arm disposed within the handle for receiving the proximal end of the elongated drive rod for longitudinal and rotational movement within the handle; and at least one stop member attached to at least one of the jaw members for controlling the distance between opposing jaw members during sealing.

3. A bipolar endoscopic instrument according to claim 2 wherein the elongated drive rod conducts a first electrical potential to one of the jaw members and the forceps includes means for conducting a second electrical potential to the other of the jaw members.

4. A bipolar endoscopic instrument according to claim 3 wherein the means for conducting a second electrical potential includes an outer tube which is electrically insulated from the elongated drive rod.

5. A bipolar endoscopic instrument according to claim 4 wherein the handle includes a rotating assembly attached to a distal end thereof, the rotating assembly mechanically cooperating with the outer tube to rotate the jaw members about a longitudinal axis disposed through the outer tube.

6. A bipolar endoscopic instrument according to claim 2 further comprising a yoke which electrically insulates the jaw members during activation and sealing.

7. A bipolar endoscopic instrument according to claim 6 wherein the yoke cooperates with the elongated drive rod to move the jaw members, the yoke including:

at least one detent which moves the jaw members from the first to second positions upon linear reciprocation of the elongated drive rod; and a pair of shoulder portions which abut the jaw members in the second position and offload pressure on the pin during clamping and sealing of tissue.

8. A bipolar endoscopic instrument according to claim 2 wherein the proximal end of the elongated drive rod includes a generally rounded head and the resilient arm includes a bifurcated distal end which forms a clevis and is dimensioned to receive the generally rounded head therein.

\* \* \* \* \*